United States Patent [19]
Schulman et al.

[11] Patent Number: 5,750,926
[45] Date of Patent: May 12, 1998

[54] HERMETICALLY SEALED ELECTRICAL FEEDTHROUGH FOR USE WITH IMPLANTABLE ELECTRONIC DEVICES

[75] Inventors: Joseph H. Schulman, Santa Clarita; Lyle Dean Canfield, Lake Hughes, both of Calif.

[73] Assignee: Alfred E. Mann Foundation for Scientific Research, Sylmar, Calif.

[21] Appl. No.: 515,559

[22] Filed: Aug. 16, 1995

[51] Int. Cl.$^6$ ........................................ H05K 5/06
[52] U.S. Cl. .................. 174/52.3; 257/698; 257/702; 257/704; 257/710
[58] Field of Search .................. 174/52.2, 52.3, 174/52.4; 257/698, 692, 693, 697, 702, 704, 710

[56] References Cited

U.S. PATENT DOCUMENTS

| | | | |
|---|---|---|---|
| 3,558,993 | 1/1971 | Rigby | 257/698 |
| 5,280,413 | 1/1994 | Pai | 361/792 |
| 5,293,069 | 3/1994 | Kato et al. | 257/698 |
| 5,381,039 | 1/1995 | Morrison | 257/701 |
| 5,397,917 | 3/1995 | Ommen et al. | 257/698 |
| 5,523,622 | 6/1996 | Harada et al. | 257/734 |

FOREIGN PATENT DOCUMENTS

| | | |
|---|---|---|
| 0266210 | 5/1988 | European Pat. Off. . |
| 8201134 | 4/1982 | WIPO . |
| 9534342 | 12/1995 | WIPO . |

Primary Examiner—Kristine L. Kincaid
Assistant Examiner—Hung V. Ngo
Attorney, Agent, or Firm—Fitch, Even, Tabin & Flannery

[57] ABSTRACT

A thin hermetically sealed electrical feedthrough suitable for implantation within living tissue permits electrical connection between electronic circuits sealed within an hermetically sealed case and electrical terminals or contacts on the outside of the case. The hermetically sealed case is made by hermetically bonding a cover to an insulating layer. The hermetically sealed electrical feedthrough is made by depositing a conductive trace on the insulating layer and then depositing another insulating layer thereover, so that the conductive trace is hermetically encapsulated within the insulating layers. At least two spaced-apart openings are formed in the insulating layers before bonding the cover thereto, exposing the conductive trace. Additional conductive material is then inserted within each of the openings or holes so as to form conductive vias that make electrical contact with the conductive trace. The cover is then hermetically sealed to the insulating layer so that at least one conductive via resides inside of an hermetically sealed cavity formed under the cover, and the other conductive via resides outside of the hermetically sealed cavity. An electrical feedthrough is thus formed through the respective conductive vias and conductive trace so that electrical contact may be made between the outside and inside of the hermetically sealed cavity.

29 Claims, 3 Drawing Sheets

HERMETICALLY SEALED ELECTRICAL FEEDTHROUGH FOR USE WITH IMPLANTABLE ELECTRONIC DEVICES

BACKGROUND OF THE INVENTION

The present invention relates to hermetically sealed feedthroughs that allow electrical connections to be made with electronic circuitry or components which are hermetically sealed in housings or cases suitable for implantation within living tissue. More particularly, the invention relates to a hybrid ceramic extremely thin film hermetic seal that permits very thin hermetically sealed housings to be formed wherein electronic circuitry may me placed and protected, yet still allow electrical contact to be readily established with such electronic circuitry through the use of thin film hermetically sealed feedthroughs.

Hermetically sealed cases or housings are widely used to protect electronic components that may be susceptible to damage or malfunction from exposure to the surrounding environment. For example, a piezoelectric crystal and certain semiconductor devices need to be protected from the atmosphere, and are thus commonly hermetically sealed in a metal can. The hermetic seal is simply an airtight, durable seal that is long-lasting and physically rugged. Sometimes the interior of an hermetically sealed enclosure is filled with an inert gas such as helium, to further retard the deterioration of the component or components inside. As no seal is perfect, the tightness of the hermetic seal, referred to as the hermeticity, is typically measured or specified in terms of the leakage rate through the seal, expressed in cc/sec. Sometimes, for very low leakage rates, the hermeticity can only be measured by placing a radioactive gas within the enclosure and then using an appropriate radiation detector to "sniff"0 the seal for radioactive leaks.

Where the electrical component or components are to be implanted in body tissue, the hermetically sealed case (which must be made from a material that is compatible with body tissue, such as platinum or stainless steel or glass) serves a dual purpose: (1) it protects the electrical component or components from body fluids and tissue, which fluids and tissue could otherwise prevent the components from performing their desired function; and (2) it protects the body tissue and fluids from the electrical component or components, which component or components may be made at least in part from materials that may be damaging to body tissue, and which therefore could pose a significant health risk to the patient wherein they are implanted. It is thus critically important that the hermetic seal of an implanted device be especially long-lasting and physically rugged. For this reason, stringent requirements are imposed on the hermeticity of an implanted device, typically requiring a seal that provides a leakage rate of less than $10^{-8}$ cc/sec.

In recent years, the size of implanted medical devices has decreased dramatically. It is now possible, for example, to construct a simple stimulator device in a small hermetically sealed glass tube that can be implanted through the lumen of a needle. See, U.S. Pat. Nos. 5,193,539; and 5,193,540, incorporated herein by reference. With such a small size comes increased requirements for the tightness of the hermetic seal because there is less empty space inside of the sealed unit to hold the moisture that eventually leaks therethrough. The hermeticity requirements of such small devices may thus be on the order of $10^{-11}$ or $10^{-12}$ cc/sec. While the small size is thus advantageous, the stringent hermeticity requirements imposed for such small devices makes them extremely difficult to manufacture, and thus increases the cost of manufacture.

A significant problem associated with an hermetically sealed package, particularly where the package is implanted in living tissue, is the feedthrough mechanism used to allow electrical conductivity between the circuits sealed in the hermetically sealed package, and the environment surrounding the enclosure. Most implanted medical devices, such as a cardiac pacemaker, neural stimulator, biochemical sensor, and the like, require such a feedthrough in order to establish electrical contact between the appropriate circuitry sealed in the hermetically closed package and an external electrode that must be in contact with the body tissue or fluids outside of the sealed package. In a pacemaker, for example, it is common to provide such a feedthrough by using a feedthrough capacitor. A representative feedthrough capacitor is described in U.S. Pat. No. 4,152,540. Alternatively, a hermetic feedthrough is typically used to establish electrical connections between the appropriate electronic components or circuitry sealed in the hermetically closed package and an external control device, or monitoring equipment.

Heretofore, an hermetic feedthrough for implantable packages has consisted of a ceramic or glass bead that is bonded chemically at its perimeter through brazing or the use of oxides, and/or mechanically bonded through compression, to the walls of the sealed package. A suitable wire or other conductor passes through the center of the bead, which wire or conductor must also be sealed to the bead through chemical bonds and/or mechanical compression. The feedthrough is thus circular, and the wire(s) or conductor(s) mounted within the bead are centered or mounted in a uniform pattern centrally positioned within the bead. Such centering is necessary due to the thermal coefficients required for the different expansion rates that occur when heating is made to either cause the compression seal or to cause the oxide or bronze bonding.

Other related art relating to methods for forming hermetically sealed cases having electrical feedthroughs and vias include U.S. Pat. No. 4,525,766 issued to Petersen, U.S. Pat. No. 4,861,641 issued to Foster et al., and U.S. Pat. No. 4,882,298 issued to Moeller et al. While these patents teach improvements in the art, such teachings are limited to use with semiconductor substrates and are not easily adaptable for use with microminiature devices implantable within living tissue.

As implantable devices have become thinner and thinner, the size of the ceramic or glass beads used for electrical feedthroughs has also become smaller and smaller. This means that the holes through the center of the glass beads have likewise become smaller and smaller, and/or that the distance between the center wire or conductor and the wall of the metal case or package has become smaller and smaller. A small distance between the conductor and the metal wall presents a problem in that an electrical short can easily occur therebetween. To prevent the possibility of such a short, which can occur, e.g, if water or other conductive fluid establishes a bridge between the wire and wall on the outside of the package, it is common to insulate the wire on the outside of the can or package with epoxy or other kinds of plastics or waxes. However, as the overall size of the components decreases, it becomes increasingly difficult to make an effective insulating seal in this manner. Further, although using ceramic packages or cases in place of metal packages or cases eliminates this problem (because the ceramic cases are non-conductive), ceramic cases are by their very nature brittle, and must thus be made thicker than metal walls. Hence, use of ceramic packages reduces the ability to make the case very thin. It is thus evident that what is needed is a way to provide a thin hermetically sealed metal package or case having an electrical feedthrough that eliminates or reduces the possibility of shorting between the feedthrough conductor and the metal wall of the package or case.

SUMMARY OF THE INVENTION

The present invention addresses the above and other needs by providing a thin film hermetically sealed feedthrough. Such feedthrough may be used in a wide variety of applications, but typically is used with a very thin hermetically sealed case or housing suitable for implantation within living tissue, thereby permitting electrical connection between electronic circuits or components sealed within the case and electrical terminals on the outside of the case.

The hermetically sealed feedthroughs and case of the present invention comprise at least one insulating layer that encapsulates and hermetically seals a metal trace. For example, a conductive trace is deposited on an upper surface of a first insulating substrate or layer. The conductive trace is then covered by depositing another insulating layer over the conductive trace so that the conductive trace is effectively sandwiched between two insulating layers. Advantageously, as the insulation layer is deposited over the metal trace, the metal trace becomes hermetically sealed within the insulating layers. As the deposition of the insulating layer is carried out over the metal trace, at least two openings (or channels) are transversely formed therethrough so as to expose different ends or portions of the conductive trace. Additional conductive material is then placed within each of the openings or channels to form conductive paths or links (hereafter "vias") that make electrical contact with the ends or portions of the conductive trace at the respective locations of the vias. A cover is then hermetically sealed or bonded to one of the insulating layers so as to form an hermetically sealed cavity, with at least one of the vias residing inside of the hermetically sealed cavity, and with at least another one of the vias residing outside of the hermetically sealed cavity. Because the via in the hermetically sealed cavity is in electrical contact by way of the conductive trace with the via on the outside of the hermetically sealed cavity, an electrical feedthrough is thus advantageously provided that allows electrical contact to be made between the via on the inside of the hermetically sealed cavity and the via on the outside of the hermetically sealed cavity. Hence, electronic circuitry or components may be mounted within the hermetically sealed cavity, and electrical contact can be established with such circuitry or components from a location outside of the hermetically sealed cavity, as required, for a given application.

In accordance with one aspect of the invention, the insulating layers that hermetically sandwich the metal trace may be deposited on a thin metal substrate, thereby allowing an extremely thin feedthrough to be made.

In accordance with another aspect of the invention, the insulating layer(s) and/or substrate are made from aluminum oxide $Al_2O_3$, or other suitable insulating material, such as magnesium oxide, zirconium oxide, or many types of glass, and may be deposited using conventional deposition techniques.

It is thus a feature of the present invention to provide an hermetically sealed thin film feedthrough.

It is another feature of the invention to provide such a hermetically sealed thin film feedthrough in combination with a thin hermetically sealed cavity wherein electronic components and/or circuitry may be housed, thereby allowing electrical connections to be established with the circuitry and/or components within the sealed cavity from a location outside of the cavity.

It is another feature of the invention to provide an extremely thin hermetically sealed housing, including hermetically sealed feedthroughs for allowing electrical contact to be established between the inside and outside of such housing, suited for protecting electronic circuitry and/or components from a hostile environment.

It is yet an additional feature of the invention to provide an extremely thin hermetically sealed housing, including hermetically sealed feedthroughs that permit electrical connections between the inside and outside of the sealing housing, especially suited for implantation in living body tissue, e.g., especially suited for implantation in animals or humans.

It is still another feature of the invention to facilitate the manufacture and use of tiny, thin hermetically sealed electrical circuits or components.

BRIEF DESCRIPTION OF DRAWINGS

The above and other aspects, features and advantages of the present invention will be more apparent from the following more particular description thereof, presented in conjunction with the following drawings wherein.

DETAILED DESCRIPTION OF THE INVENTION

The following description includes several embodiments of the hermetically sealed case and hermetic feedthroughs for use with implantable electronic devices and collectively is a description of the best mode presently contemplated for carrying out the invention. This description is not to be taken in a limiting sense, but is made merely for the purpose of describing the general principles of the invention. The scope of the invention should be determined with reference to the claims.

Figure 1:
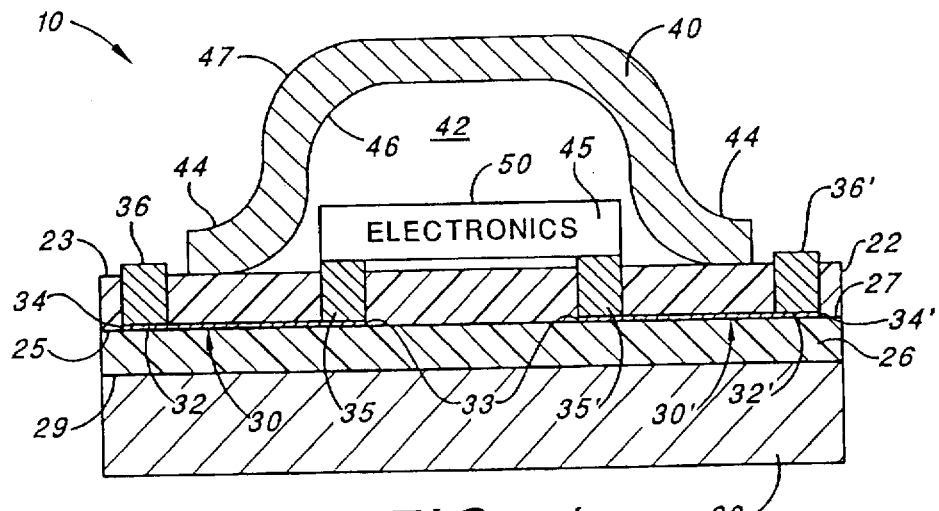
FIG. 1 is a side, cross sectional view of the embodiment of the hermetically sealed case and hermetic feedthroughs for implantable electronic devices in accordance with the present invention.

As shown in FIG. 1, a first embodiment of the hermetically sealed case 10 for an implantable electronic device includes a substrate 20 (which may or may not be insulating), two insulating layers 22 and 26, one or more hermetic feedthroughs 30, and a cover 40. In this first embodiment, a first insulating layer 26, preferably made from aluminum oxide $Al_2 O_3$ or other suitable insulating material such as magnesium oxide or zirconium oxide, is deposited on a selected substrate 20, using conventional deposition techniques. (It is noted that the substrate 20, if insulating, may serve the function of the first insulating layer 26.) One method of depositing the insulating layer, for example, is to use ion enhanced evaporated sputtering of aluminum oxide. Advantageously, ion enhanced evaporated sputtering of aluminum oxide, or magnesium oxide, or zirconium oxide, forms a high quality insulation layer.

A metalized pattern or trace of a suitable conductive material 32 is then deposited on the upper surface 27 of the first insulating layer 26, the lower surface 29 of the first insulating layer 26 being adjacent to the substrate 20. (In those instances where the substrate 20 is already an insulator, the metalized trace 32 may be deposited directly on an upper surface of the substrate 20, which substrate then serves the function of the first insulating layer 26.) The metalized trace or pattern may be deposited on the insulating layer 26 using conventional techniques as are well known in the art.

A second insulating layer 22, having an upper surface 23 and lower surface 25 is then deposited over the conductive material 32 and the first insulating layer 26 using conventional deposition techniques. The conductive material 32 is thus sandwiched between the lower surface 25 of the second insulating layer 22 and the upper surface 27 of the first insulating layer 26, thereby encapsulating the trace of conductive material 32 within insulating material.

At least two openings are formed through the second insulating layer 22 to expose the trace of conductive material 32. Such openings may be formed using conventional semiconductor processing techniques. For example, portions of the first insulating layer 26 and/or trace of conductive material 32 may be masked as the second insulating layer 22 is sputtered (or otherwise deposited) onto the first insulating layer 26 and conductive material 32. One of the openings may be formed in the second insulating layer 22 at or near an interior end 33 of the conductive material, while another of the openings may be formed in the second insulating layer 22 proximate an exterior end 34 of the conductive material 32. Such openings are then filled with a suitable conductive metal, such as platinum or tungsten, that forms an interior conductive via 35 and an exterior conductive via 36 at the respective ends 33 and 34 of the conductive trace 32.

A similar conductive trace 3', with interior conductive via 35' and exterior conductive via 36' may similarly be formed on another area of the substrate 20, as needed or desired. Electronic circuitry 45 may then be positioned near the interior portion of the substrate and electrically connected to the interior conductive vias 35, 35' in conventional manner.

An important feature of the invention is that the deposition processes used to cover or sandwich the metal trace with an insulating layer(s) also hermetically seals the metal trace, i.e., completely encapsulates the metal trace within the insulating material. Further, even at the boundary of the metal trace with the insulating layer(s), an effective hermetic seal is created. The metal trace remains hermetically sealed at all locations except possibly at the point where the openings or holes are made for the vias. That is, some leakage may occur through the via from one layer to the next. (This is because the via may not be, and indeed does not have to be, perfectly plugged with a conductive material that is added after the opening or hole is made. Moreover, even it were completely plugged, there would still likely be some leakage around the edges of the via.) However, such leakage through the via is blocked at the intersection of the via with the next layer. As a result, there is no leakage between, e.g., via 36 and via 35, even though there may be some leakage through via 36 between the upper surface 23 of layer 22 and the lower surface 25 of the layer 22. The lower surface 25 of layer 22 is hermetically sealed to the metal trace 30 and to the upper surface 34 of the next layer 26, so the hermetic seal is preserved.

A metal cover 40, e.g., formed to have a cross section like that of a top hat, provides a cavity 42 under its center area with flat edges 44 therearound. The flat edges 44 are designed to be tightly bonded to the upper surface of the second insulating layer 22, thereby sealing the cavity 42. The interior conductive vias 35, 35', and electronic circuitry 45, are positioned to reside within of the cavity 42 formed by the metal cover 40, while the other exterior conductive vias 36, 36' reside outside of the metal cover 40, and hence outside of the sealed cavity 42. An electrical path, or "electrical feedthrough" is thus provided between the outside of the sealed cavity 42 and the inside of the sealed cavity 42 through the respective conductive vias 35,36 and the conductive trace 32, and/or the respective conductive vias 35', 36' and the conductive trace 32'. Thus, electrical contact may be made with electronic circuitry 50, or other electrical devices, e.g., sensors or temperature probes, mounted and hermetically sealed within the cavity 42.

In accordance with one aspect of the invention, the thinness of the hermetically sealed case is facilitated, in the first embodiment, by making the substrate from a thin metal wall. The metal wall may be, e.g., on the order of 0.002 to 0.010 inches thick. For example, if the wall is, e.g., 0.004 inches thick (4 mils), and assuming that aluminum oxide layers are used that are only on the order of 0.25 mils thick, and also assuming that the metal cover is also about 4 mils thick, it is thus possible to construct an hermetically sealed case that is only about 8.5–9.0 mils thick at its edges, and only as thick at its center as is required to form a cavity between the metal walls that houses appropriate electrical components.

Note that the insulating layers will typically have a thickness less than 1 mil, e.g., 0.25 mils.

Figure 2:
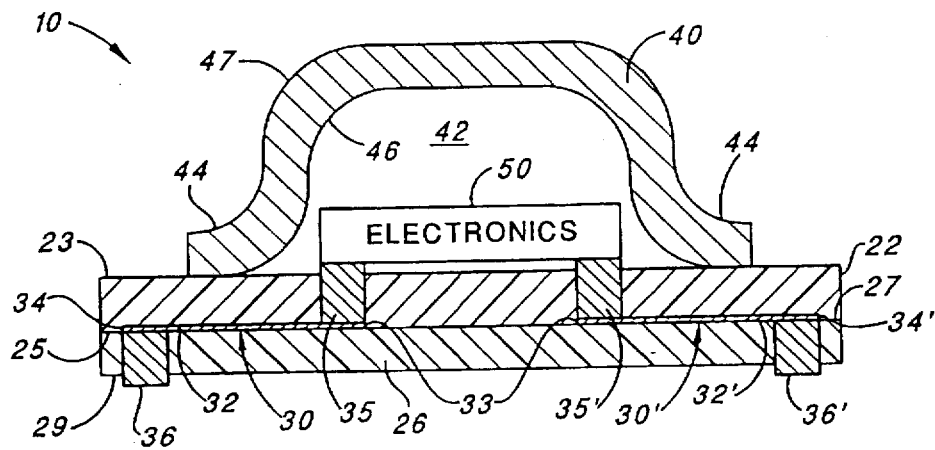
FIG. 2 is a side, cross sectional view of another embodiment of the hermetically sealed case and hermetic feedthroughs for implantable electronic devices in accordance with the present invention.

Referring to FIG. 2, another embodiment of the hermetically sealed case 10 and hermetic feedthroughs 30 for implantable electronic devices is shown. This embodiment is similar to the previously described embodiment, however, the plurality of openings or vias are not confined to pass through only the second insulating layer 22. Much like the prior embodiment, this embodiment includes at least two insulating layers 22 and 26, preferably made from aluminum oxide $Al_2O_3$, zirconium oxide $Zr_2O_3$, magnesium oxide $Mg_2O_3$, or another suitable insulating material. A metalized pattern or trace of a suitable conductive material 32 is deposited on the first insulating layer 26. The second insulating layer 22 is then deposited over the conductive material 32 and the first insulating layer 26.

The plurality of vias or openings are formed in either or both of the insulating layers 22 and 26 at preselected locations proximate to the pattern of conductive material or trace 32, 32' in order to communicate and expose the conductive trace 32 or 32'. As seen in FIG. 2, one of the openings is provided on the first insulating layer 26, while a second opening is provided on the second insulating layer 22. Both openings, however, are situated to be in communication with the metalized trace 32 deposited on the first insulating layer and between the upper surface 27 of the first insulating layer 26 and the lower surface 25 of the second insulating layer 22. The multiple openings are then filled with a suitable conductive material that forms the conductive vias 35, 35' and 36, 36' which establish an electrical communication with the pattern of conductive material 32.

A metal cover 40 is then placed over one or more of the conductive vias 35, 35' and hermetically bonded to the appropriate insulating layer. As seen in FIG. 2, the metal cover 40 is disposed over interior conductive vias 35, 35' and hermetically bonded to the upper surface 23 of the second insulating layer 22. The metal cover 40 is preferably shaped such that it forms a hermetic cavity 42 immediately above the interior conductive vias 35, 35'. In addition, the metal cover 40 is situated such that it shrouds the electronic components 50, or other circuitry, of the implantable device. The interior conductive vias 35, 35' are further connected to the electronics 50, as required.

The arrangement shown in FIG. 2 provides that at least two interior conductive vias 35, 35' are exposed within the interior 46 of the hermetically sealed cavity 42 formed under the cover 40, while the exterior conductive vias 36, 36' are exposed outside of the hermetically sealed cavity 42 and on the opposite surface from the hermetically sealed cavity 42 as the lower surface 29 of the first insulating layer 22. An electrical path, or hermetic feedthrough 30 is thus formed through the respective conductive vias 35, 36, and conductive trace 32, as well as through the conductive vias 35', 36' and the conductive trace 32', so that electrical continuity is provided between the outside and inside of the hermetically sealed case 10 and on opposite surfaces 23,29 of the adjoining insulating layers 22,26.

Figure 3:
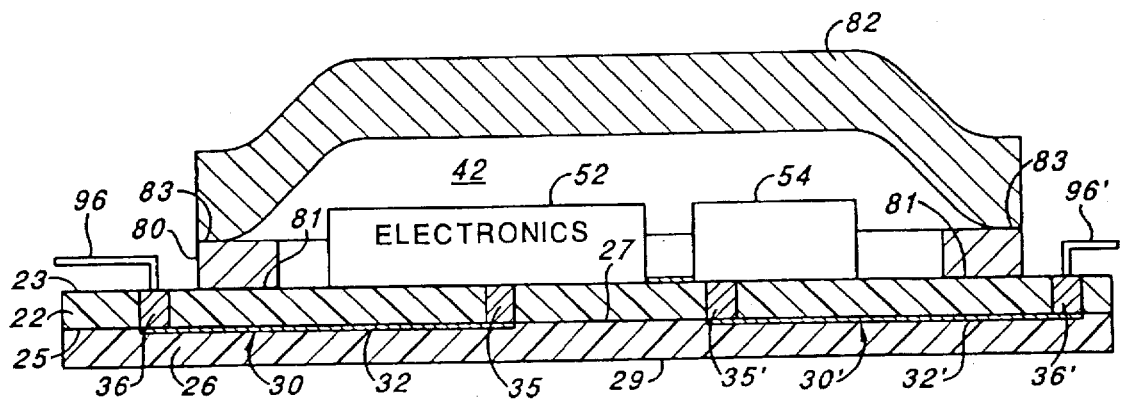
FIG. 3 is a side, cross sectional view of still another embodiment of the hermetically sealed case and hermetic feedthroughs for implantable electronic devices in accordance with the present invention.

Turning next to FIG. 3, yet another embodiment of a hermetically sealed case 10 for implantable electronic devices is shown. The embodiment shown in FIG. 3 is comprised of a plurality of layers of insulating material 22,26, and a frame 80 to which a lid 82 has having been hermetically sealed. The electrical components 50, or other circuits, which include components such as silicon chips 52 and/or energy storage devices 54, are connected to external leads 96, 96' by hermetic feedthroughs 30, 30' which permit the flow of electrical currents through the case 10 while maintaining hermeticity. Various metalized patterns of a suitable conductive material 32, 32' such as gold (Au), platinum (Pt), or tungsten (W), or alloys thereof, are deposited between the insulating layers 22, 26 to form the electrical circuits and connections necessary for the implanted device to operate.

Specifically, the frame 80 is disposed on the upper surface 23 of the uppermost insulating layer 22 and surrounds the electronics 50 which preferably include a silicon chip 52 and the energy storage device 54 such as a capacitor. The insulating layers 22, 26 are preferably made from a thin layers of aluminum oxide $Al_2O_3$ or zirconium oxide $Zr_2O_3$ or magnesium oxide $Mg_2O_3$ or glass. The frame 80 is fabricated from a body-safe metal, and is preferably a thin structure properly dimensioned to surround the electronics 50. The frame material is preferably selected from those metals or alloys that readily form an instant oxide when heated, or when exposed to air or oxygen, i.e., that readily oxidize when heated in and/or exposed to an oxygen-containing atmosphere. It is important that the frame material and the insulating material have thermal coefficients of expansion that are approximately equal. This minimizes the risk of cracking when the frame 80 and the uppermost insulating layer 22 are bonded together at high temperature and then cooled. The frame 80, for example, may be made from an alloy of Titanium-Niobium (i.e., Ti and Nb), which is available from commercial sources. Advantageously, both the preferred aluminum oxide insulating layer and the Titanium-Niobium alloy frame have thermal coefficients of expansion of between $6 \times 10^{-6}$ and $10 \times 10^{-6}$/°C.

The frame 80 and the uppermost insulating layer 22 are secured together by preferably forming a hermetically sealed, solderless bond between the insulating layer 22 and the frame 80. The preferred method of forming the bond is a diffusion bonding technique. This bonding technique involves the combination of high temperature, and high pressure in an inert atmosphere to bring the surfaces of the frame 80 and the uppermost insulating layer 22 together such that the titanium atoms fill the voids at the interface or diffusion bonding site 81 to adhere the frame 80 with the insulating layer 22. A method and apparatus for brazeless ceramic to metal bonding used in implantable devices is more fully disclosed in co-pending U.S. patent application Ser. No. 08/319,580, filed Oct. 7, 1994 entitled Brazeless Ceramic-to-Metal Bond, attached as Appendix A, and incorporated herein by reference.

The lid 82 is also made from bio-compatible and corrosion resistant body-safe metals typically used for implantable devices such as titanium, stainless steel or cobalt-chromium alloys, although titanium is preferred. The lid 82 is disposed on the frame 80 and forming the cavity 42 and covering the electronics 50 with a minimum of clearance therein. The lid 82 is preferably laser welded to the frame 80. The laser weld sites 83 as well as the diffusion bonding sites 81 may then be further encapsulated or shrouded within an epoxy sealant 95 or other protective coatings or membranes (not shown).

It is noted that the above description of the materials that may be used for the embodiment of the invention shown in FIG. 3 also applies to the other embodiments of the invention, e.g., those of FIGS. 1, 2 and 4–5.

Figure 4:
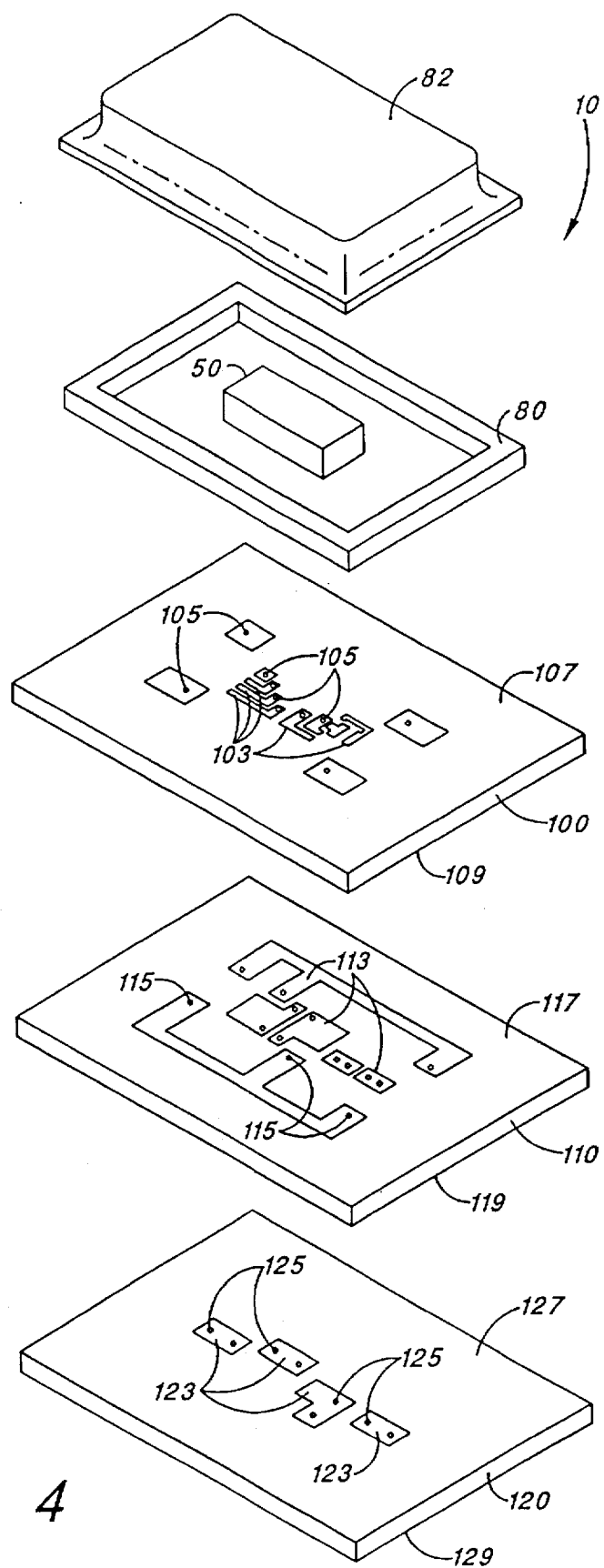
FIG. 4 is an exploded perspective view of yet another embodiment of the present invention illustrating the arrangement of a hermetically sealed case and hermetic feedthroughs for an implantable bio-chemical sensor comprising a plurality of insulating layers and a plurality of hermetic feedthroughs.
Figure 5:
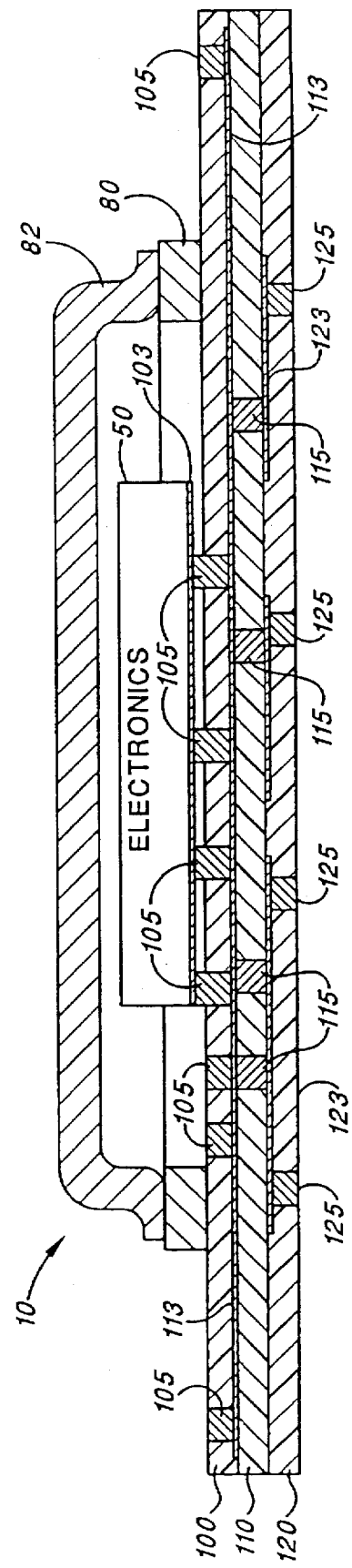
FIG. 5 is a side, cross sectional view of the embodiment of FIG. 4 illustrating the plurality of insulating layers and a plurality of hermetic feedthroughs.

FIG. 4 and FIG. 5 illustrate yet another embodiment of the hermetically sealed case 10 having multiple hermetic feedthroughs 30 for use in implantable electronic devices. FIG. 4 is an exploded perspective view of such other embodiment, while FIG. 5 is a side, cross-sectional view of such embodiment. As seen best in FIG. 4, the embodiment includes three individual insulating layers 100, 110, and 120 with a plurality of metalized patterns 103, 113, 123, and 133 and conductive openings or vias 105, 115, and 125 disposed therein. The embodiment of FIGS. 4–5 further includes a frame 80, metal lid 82, and associated electronics 50, which may be the same as described in previous embodiments.

The individual substrate layers or insulating layers each have elongated upper and lower planar surfaces with specialized metalized pattern formed thereon. These individual substrate layers are aligned and successively layered so as to form an implantable device having both internal and external electrical connections.

FIG. 4, for example, shows a first or top insulating layer 100 having a plurality of metalized patterns 103 representing various electrical connections or circuitry. The top insulating layer 100 also has a plurality of holes or openings that have been filled with a suitable conductive material, e.g., a metal, to form a plurality of conductive vias 105. Each of the conductive vias 105 are formed at preselected locations proximate the metalized patterns 103 and in electrical contact therewith. The conductive vias 105 extend in a vertical direction from the upper surface 107 to the lower surface 109 and provide predetermined electrical connections from the electronic components 50 and metalized patterns 103 on the top insulating layer 100 to the adjacent intermediate layer 110.

The intermediate layer 110 also has a plurality of independent metalized patterns 113 deposited on an upper surface 117. As seen in FIGS. 4–5, the intermediate insulating layer 110 is aligned with the top insulating layer 100 such that the conductive vias 105 of the top insulating layer 100 are in electrical contact with the metalized patterns 113 on the intermediate insulating layer 110. Such alignment is generally represented by the target areas outlined on the intermediate insulating layer 110. The intermediate insulating layer 110 also has a plurality of conductive vias 115 which extend from the upper surface 117 to the lower surface 119 that represent electrical paths or conduits which are adapted to provide electrical connections to the adjacent insulating layer 120 immediately below the intermediate insulating layer 110.

A bottom insulating layer 120 is aligned with the intermediate insulating layer 110 such that the conductive vias 115 of the intermediate insulating layer 110 are in electrical contact with the metalized patterns 123 on the upper surface 127 of the bottom insulating layer 120. As before, such alignment is generally represented by the target areas outlined on the upper surface 127 of the bottom insulating layer 120. Much like the two prior insulating layers, the bottom insulating layer 120 also has a plurality of independent metalized patterns deposited on the upper surface 127 and a plurality of openings which have been filled with a suitable conductive material to form conductive vias 125. The conductive vias 125 represent electrical paths or conduits which are aligned to provide vertical electrical connections to whatever metalized patterns may be required on the lower surface (not visible in FIG. 4) of the bottom insulating layer 120.

As seen in the embodiment of FIGS. 4 and 5, such embodiment is comprised of a plurality of layers of insulating material 100, 110, 120, a frame 80 and a lid 82 having been hermetically sealed together. Although only three insulating layers and six hermetic paths are shown, it is readily apparent that any number of insulating layers and hermetic paths can be aligned, connected, and covered in the manner described above to provide the hermetic feedthroughs required in many implantable devices. As in the prior embodiments, the frame 80 is preferably diffusion bonded to the uppermost insulating layer 100 utilizing the brazeless bonding technique hereinbefore described, but it is to be understood that any suitable bonding technique may be used for this purpose. The lid 82 is preferably laser welded to the frame 80. The laser weld sites as well as the diffusion bonding sites may then be further encapsulated or shrouded within an epoxy sealant 95.

As indicated above, the preferred method of depositing the insulating layers is using ion enhanced evaporated sputtering of aluminum oxide, magnesium oxide or zirconium oxide so as to form a high quality insulation layer over the target substrate or other material. A hybrid ceramic may also be used as one or more of the insulating layers. The openings may then be formed, e.g., by masking portions of any underlying metalized patterns as the insulating layer is being deposited. The openings or holes are then filled with a suitable conductive metal such as platinum or gold or tungsten to form the conductive vias. The aforementioned metalized patterns or traces are deposited or etched on the insulating layers using conventional thin film deposition, or metalized etching techniques, as are common in the printed circuit board and integrated circuit fabrication arts.

In all of the above described embodiments of the present invention, the hermetically sealed cases and hermetic feedthroughs can be made extremely thin. In fact, the constituent parts of the described embodiments can be on the order of a mil or a few mils thick. For example, using currently known processing techniques, the frame and lid can be as thin as approximately 4 mils. The height of the cavity can be as small as about between 5 to 10 mils depending on the connections of the electronics contained within the cavity. The insulating layers, as indicated above, can be on the order of less than 1 mil thick, it is thus feasible using presently available processing techniques to construct an implantable device less than 25 mils thick, yet still providing an hermetically sealed case and hermetic feedthroughs. As processing techniques improve, the such dimensions will be even smaller.

From the foregoing, it should be appreciated that the present invention thus provides an improved hermetically sealed case having hermetic feedthroughs. Further, it will be apparent that various changes may be made in the form, construction and arrangement of the elements thereof without departing from the spirit and scope of the invention or sacrificing all of its material advantages, the forms hereinbefore described being merely exemplary embodiments thereof. Therefore, it is not intended that the scope of the invention be limited to the specific embodiments described. Rather, it is intended that the scope of this invention be determined by the appended claims or their equivalents.

What is claimed is:

1. An electrical feedthrough suitable for implantation within living tissue comprising:

a metal trace encapsulated within an insulating material so as to form a hermetic seal between the metal trace and the insulating material, the insulating material and metal trace being made from materials that are compatible with living tissue, and the hermetic seal being hermetic in a living tissue environment; and first and second conductive vias that pass through the insulating material from an outer surface thereof to make electrical contact with the metal trace at respective spaced-apart locations along the metal trace, said first and second conductive vias including conductive material that is also compatible with living tissue.

2. The electrical feedthrough of claim 1 further including a cover hermetically bonded to a portion of the insulating material so as to define a hermetically sealed cavity under the cover, one of the first or second conductive vias being positioned inside of said cavity, and the other of the first or second conductive vias being positioned outside of said cavity, whereby electrical contact may be made to the inside of the cavity from a location outside of the cavity.

3. The electrical feedthrough of claim 2 wherein said insulating material comprises an insulating substrate onto which the metal trace is deposited and over which an insulating layer is deposited.

4. The electrical feedthrough of claim 2 further including a substrate, and wherein said insulating material comprises a first insulating layer and a second insulating layer, the first insulating layer being deposited over a surface of the substrate, the metal trace being deposited on the first insulating layer, and the second insulating layer being deposited over the metal trace and first insulating layer.

5. The electrical feedthrough of claim 4 wherein said substrate comprises a metal having a thickness no greater than about 0.010 inches.

6. The electrical feedthrough of claim 1 wherein the insulating material is selected from the group consisting of: aluminum oxides, zirconium oxides, magnesium oxides, and glass.

7. The electrical feedthrough of claim 1 wherein the insulating material has a thickness no greater than about 0.001 inches (1 mil).

8. The electrical feedthrough of claim 7 wherein the insulating material comprises aluminum oxide $Al_2O_3$ and has a thickness of between about 0.25 mils to 1.0 mil as measured from the metal trace to an outer surface of the insulating material.

9. The electrical feedthrough of claim 1 wherein:
   the first conductive via comprises an opening in the insulating material that exposes a point on the metal trace, and a first conductor that passes through the opening to make electrical contact with the metal trace; and
   the second conductive via comprises another opening in the insulating material that exposes another point on the metal trace, and a second conductor that passes through the other opening to make electrical contact with the metal trace.

10. The electrical feedthrough of claim 9 wherein the metal trace, the first conductor, and the second conductor each includes a material selected from the group comprising: gold, platinum, tungsten, titanium, titanium-niobium alloys, stainless steel, and cobalt-chromium alloys.

11. A hermetically sealed electrical feedthrough suitable for implantation within living tissue comprising:
   a plurality of insulating layers, each of the plurality of insulating layers being successively stacked with and hermetically bonded to an adjacent one of the plurality of insulating layers;
   a plurality of vias passing transversely through at least one of the plurality of insulating layers;
   a conductive trace placed on one of the plurality of insulating layers, the conductive trace being in electrical contact with at least two of the plurality of vias, and being hermetically bonded to the at least one of the plurality of insulating layers and to the adjacent one of the plurality of insulating layers;
   each of said plurality of vias comprising a conductor that makes electrical contact with the conductive trace; and
   a cover hermetically bonded to one of the plurality of insulating layers to form a hermetically sealed cavity, wherein one of the plurality of vias resides inside the hermetically sealed cavity, and wherein another of the plurality of vias resides outside the hermetically sealed cavity;
   whereby electrical contact may be made through the other of the plurality of vias outside of the hermetically sealed cavity with the one of the plurality of vias inside of the hermetically sealed cavity through the conductive trace.

12. The hermetically sealed electrical feedthrough as set forth in claim 11 wherein the plurality of insulating layers comprises:
   a first insulating layer having the conductive trace deposited thereon; and
   a second insulating layer deposited over the conductive trace and the first insulating layer, the one of the plurality of vias including a first opening and the other of the plurality of vias including a second opening, the first opening and the second opening expose, respectively, a first point and a second point on the conductive trace.

13. The hermetically sealed electrical feedthrough as set forth in claim 12 wherein the cover comprises a metal, and further comprises a flange around a periphery of the cover, and a formed raised portion at a center of the cover.

14. The hermetically sealed electrical feedthrough as set forth in claim 13 further comprising at least one electrical component mounted within the hermetically sealed cavity and electrically connected to the one of the plurality of vias inside the hermetically sealed cavity.

15. The hermetically sealed electrical feedthrough as set forth in claim 11 wherein each of the plurality of insulating layers comprise ceramic materials selected from the group consisting of aluminum oxides, zirconium oxides, magnesium oxides, and glass.

16. The hermetically sealed electrical feedthrough as set forth in claim 11 wherein the plurality of insulating layers comprises:
   a first insulating layer having the conductive trace deposited thereon, said other of said plurality of vias passing transversely through the first insulating layer; and
   a second insulating layer deposited over the conductive trace and the first insulating layer, said one of said plurality of vias passing transversely through the second insulating layer.

17. The hermetically sealed electrical feedthrough as set forth in claim 16 wherein the cover comprises a metal, and further comprises a flange around a periphery of the cover and a formed raised portion at a center of the cover.

18. The hermetically sealed electrical feedthrough as set forth in claim 11 wherein the cover further comprises:
   a frame hermetically bonded to the one of the plurality of insulating layers; and
   a lid hermetically bonded to the frame,
   the lid and frame thereby defining the hermetically sealed cavity, the thermal coefficients of expansion of the frame and each of the plurality of insulating layers being approximately equal.

19. The hermetically sealed electrical feedthrough as set forth in claim 18 wherein the frame further comprises a Titanium-Niobium alloy and wherein each of said plurality of insulating layers is formed from a ceramic material selected from the group consisting of aluminum oxides, zirconium oxides, magnesium oxides and glass.

20. The hermetically sealed electrical feedthrough as set forth in claim 19 wherein the frame is hermetically bonded to the one of the plurality of insulating layers using a brazeless ceramic to metal diffusion bonding technique.

21. The hermetically sealed electrical feedthrough as set forth in claim 18 wherein the lid is formed from a body-safe metal selected from the group consisting of titanium, stainless steel and cobalt-chromium alloys.

22. The hermetically sealed electrical feedthrough as set forth in claim 18 wherein any bonded portions of the lid, frame and insulating layers are further encapsulated or shrouded within an epoxy sealant.

23. The hermetically sealed electrical feedthrough as set forth in claim 11 further comprising at least one conductive trace deposited on each of said plurality of insulating layers, each conductive trace being in communication with at least two of said plurality of vias, thereby providing a plurality of electrical paths that provide a network of hermetic electrical feedthroughs between vias on the inside of the hermetically sealed cavity and vias on the outside of the hermetically sealed cavity.

24. A hermetically sealed electrical feedthrough suitable for implantation within living tissue comprising:
   a substrate;
   a first insulating layer deposited on the substrate;
   a conductive trace deposited on the first insulating layer, the conductive trace having a first end and a second end;
   a second insulating layer hermetically bonded to the conductive trace and the first insulating layer to form a hermetic seal, the hermetic seal being hermetic in a living tissue environment, the second insulating layer having first and second openings therethrough that expose the conductive trace at the first and second ends, respectively;

a first conductor within the first opening and in electrical contact with the conductive trace a second conductor within the second opening and in electrical contact with the conductive trace, the first conductor and the second conductor thus forming a first conductive via and a second conductive via, respectively; and a cover comprising a flange around a periphery of the cover and a formed raised portion at a center of the cover, the flange being hermetically bonded to the second insulating layer such that the first conductive via resides inside of a hermetically sealed cavity, and the second conductive via resides outside of the hermetically sealed cavity.

25. The hermetically sealed electrical feedthrough as set forth in claim 24 wherein the first insulating layer and the second insulating layer are formed from ceramic material selected from the group consisting of aluminum oxides, zirconium oxides, magnesium oxides, and glass.

26. The hermetically sealed electrical feedthrough as set forth in claim 25 further comprising at least one electrical component mounted within the hermetically sealed cavity and electrically connected to the first conductive via.

27. A hermetically sealed electrical feedthrough suitable for implantation within living tissue comprising:

a first insulating layer having a conductive trace deposited thereon, the first insulating layer having a first via therethrough that electrically communicates with the conductive trace;

a second insulating layer hermetically bonded to the conductive trace and the first insulating layer to form a hermetic seal, the hermetic seal being hermetic in a living tissue environment, the second insulating layer having a second via therethrough that electrically communicates with the conductive trace; and a cover comprising a flange at a periphery of the cover and a formed raised portion at a center of the cover, the flange being hermetically bonded to one of the first and second insulating layers such that one of the first and second vias resides inside of a hermetically sealed cavity formed under the formed raised portion of the cover, and the other of the first and second vias resides outside of the hermetically sealed cavity.

28. The hermetically sealed electrical feedthrough as set forth in claim 27 wherein the first insulating layer and the second insulating layer each comprise a material selected from the group consisting of aluminum oxide, zirconium oxide, and magnesium oxide.

29. The hermetically sealed electrical feedthrough as set forth in claim 28 further comprising at least one electrical component mounted within the hermetically sealed cavity, said at least one electrical component being electrically connected to the one of the first and second vias.

* * * * *